(12) United States Patent
Yamanaka

(10) Patent No.: US 11,129,517 B2
(45) Date of Patent: Sep. 28, 2021

(54) ENDOSCOPIC TREATMENT TOOL

(71) Applicant: OLYMPUS CORPORATION, Hachioji (JP)

(72) Inventor: Kazuya Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 391 days.

(21) Appl. No.: 16/130,205

(22) Filed: Sep. 13, 2018

(65) Prior Publication Data

US 2019/0008364 A1  Jan. 10, 2019

Related U.S. Application Data

(63) Continuation of application No. PCT/JP2016/061636, filed on Mar. 31, 2016.

(51) Int. Cl.
*A61M 25/00* (2006.01)
*A61M 25/01* (2006.01)
(Continued)

(52) U.S. Cl.
CPC .......... *A61B 1/00087* (2013.01); *A61B 1/018* (2013.01); *A61M 25/00* (2013.01);
(Continued)

(58) Field of Classification Search
CPC . A61B 1/00087; A61B 1/018; A61B 1/00147; A61B 10/0275; A61B 88/49;
(Continued)

(56) References Cited

U.S. PATENT DOCUMENTS 7,022,133 B2 * 4/2006 Yee ...................... A61M 25/00
623/1.11
2003/0233043 A1 * 12/2003 Windheuser ...... A61M 25/0172
600/434

FOREIGN PATENT DOCUMENTS

CN  102905632 A   1/2013
JP  H11-267226 A   10/1999
(Continued)

OTHER PUBLICATIONS

Jul. 26, 2016 International Search Report issued in International Patent Application No. PCT/JP2016/061636.
(Continued)

*Primary Examiner* — John P Leubecker
(74) *Attorney, Agent, or Firm* — Oliff PLC

(57) ABSTRACT

An endoscopic treatment tool includes a port, a sheath having a proximal region inserted into the port and a distal region continuing to the proximal region to extend to the outside of the port, a flap having a distal end in the distal region and a proximal end in the proximal region and extending in a longitudinal axis direction of the sheath from a distal end to a proximal end of the sheath, a notch surface formed in the sheath between the proximal end of the flap and the proximal end of the sheath to form a notch shape in the flap along the longitudinal axis, and a rotation preventing portion disposed between the notch surface and the internal surface of the port, wherein the rotation preventing portion has an inclined surface inclined from the opening toward the lumen and an engaging surface capable of engaging with the notch surface.

11 Claims, 14 Drawing Sheets

(51) Int. Cl.
  *A61B 1/018* (2006.01)
  *A61B 1/00* (2006.01)
  *A61B 10/02* (2006.01)
(52) U.S. Cl.
  CPC ......... *A61M 25/01* (2013.01); *A61B 1/00147* (2013.01); *A61B 10/0275* (2013.01); *A61M 25/0015* (2013.01)
(58) Field of Classification Search
  CPC .. A61M 25/00; A61M 25/01; A61M 25/0015; A61M 2025/0188; A61M 2025/018; A61M 2025/0097
  See application file for complete search history.

(56) References Cited

FOREIGN PATENT DOCUMENTS

| JP | 2002-514099 | A | 5/2002 | |
| JP | 2002-543938 | A | 12/2002 | |
| JP | 3174025 | U | * 3/2012 | ............. A47B 88/49 |
| JP | 3199259 | U | 8/2015 | |
| WO | 98/10820 | A1 | 3/1998 | |
| WO | 00/69500 | A1 | 11/2000 | |
| WO | 2015/133432 | A1 | 9/2015 | |
| WO | 2016/009690 | A1 | 1/2016 | |

OTHER PUBLICATIONS

Oct. 24, 2017 Japanese Office Action issued in Patent Application No. 2017-526146.
Nov. 20, 2020 Office Action issued in Chinese Patent Application No. 201680084056.7.
May 18, 2020 Office Action issued in Chinese Patent Application No. 201680084056.7.

* cited by examiner

ENDOSCOPIC TREATMENT TOOL

This application is a continuation application based on a PCT International Application No. PCT/2016/061636, filed on Mar. 31, 2016. The content of the PCT International Application is incorporated herein by reference.

BACKGROUND OF THE INVENTION

Field of the Invention

The present invention relates to an endoscopic treatment tool.

Description of Related Art

The endoscopic retrograde cholangiopancreatography (ERCP) is known as an inspection and a treatment using an endoscope. During the procedures of the ERCP, a guidewire is used for inserting a catheter into the biliary and pancreatic ducts to inject a contrast medium inside the biliary and pancreatic ducts.

Published Japanese Translation No. 2002-543938 of the PCT International Publication discloses an insertion tool for facilitating an insertion of a guidewire into a lumen of a catheter to be easy, wherein the guidewire is insertable into the lumen of the catheter. The insertion tool disclosed in Published Japanese Translation No. 2002-543938 of the PCT International Publication has a main lumen and a funnel lumen communicating with the lumen into which the guidewire is insertable. Furthermore, the insertion tool disclosed in Patent Document 1 has a slot (gap) with a dimension such that it is possible to insert the guidewire into the funnel lumen and remove the guidewire from the funnel lumen.

The lumen of the catheter to which the insertion tool disclosed in Published Japanese Translation No. 2002-543938 of the PCT International Publication is attached has an opening on an external peripheral surface of the catheter such that the guidewire can be removed in a radial direction of the catheter. In the state in which the insertion tool disclosed in Published Japanese Translation No. 2002-543938 of the PCT International Publication is attached to the catheter, the guidewire can be removed from the inside of the lumen in the radial direction of the catheter, and further the guidewire can removed from the funnel lumen via the slot.

SUMMARY OF THE INVENTION

According to a first aspect of the present invention, an endoscopic treatment tool includes a port having an internal surface, an external surface, and an opening configured to communicate the internal surface to the external surface; a sheath having a proximal region inserted into the port and a distal region continuing to the proximal region to extend to the outside of the port, the sheath having a lumen formed with an inner diameter larger than an outer diameter of a guidewire; a flap having a distal end in the distal region and a proximal end in the proximal region, the flap extending in a longitudinal axis direction of the sheath from a distal end to a proximal end of the sheath, and a slit formed to communicate the lumen to an external side of the sheath; a notch surface formed in the sheath between the proximal end of the flap and the proximal end of the sheath to form an opening along the longitudinal axis of the sheath such that a notch shape is formed in the flap; and a rotation preventing portion having an inclined surface inclined from the opening of the port toward the lumen and an engaging surface configured to engage with the notch surface.

According to a second aspect of the present invention, in the endoscopic treatment tool according to the first aspect, at least part of the rotation preventing portion may be configured to form an edge of the opening of the port for inserting the guidewire into the lumen.

According to a third aspect of the present invention, in the endoscopic treatment tool according to the first aspect, the port may be fixed to the proximal region of the sheath such that the proximal region of the sheath is formed in a straight shape, the opening of the port may be extended to a distal end surface of the port, the proximal region of the sheath may include a first region in which the notch surface is formed; and a second region formed in a substantial tubular shape from a distal end of the notch surface to the distal end surface of the port, and the second region may be configured to communicate with the opening of the port in the radial direction of the sheath.

According to a fourth aspect of the present invention, in the endoscopic treatment tool according to the first aspect, the rotation preventing portion may be configured to restrict a movement of the notch surface in a rotation direction around the longitudinal axis of the sheath.

According to a fifth aspect of the present invention, in the endoscopic treatment tool according to the first aspect, a groove may be formed in part of the port, and at least part of the rotation preventing portion may be formed in a shape fitted into the groove.

According to a sixth aspect of the present invention, in the endoscopic treatment tool according to the first aspect, the rotation preventing portion may have a gap communicating with the opening of the port.

According to a seventh aspect of the present invention, in the endoscopic treatment tool according to the first aspect, the rotation preventing portion may have an elastic portion inserted into a space between an external peripheral surface of the sheath and the internal surface.

According to an eighth aspect of the present invention, in the endoscopic treatment tool according to the seventh aspect, the elastic portion may be configured to extend between an external peripheral surface of the second region and the internal surface, and the elastic portion may be positioned at the distal end of the rotation preventing portion.

According to a ninth aspect of the present invention, in the endoscopic treatment tool according to the seventh aspect, the opening of the port may be formed such that an opening width gradually increases toward the distal end surface of the port in a range more distal than a distal end of the elastic portion.

According to a tenth aspect of the present invention, in the endoscopic treatment tool according to the seventh aspect, a width of the slit may be smaller than the outer diameter of the guidewire, at least part of the elastic portion may be disposed at both sides of the slit at a position on a side of the opening of the port with respect to a center axis of the lumen, and at least part of the elastic portion may be configured to bias the flap inwardly in the radial direction such that the width of the slit becomes smaller than the outer diameter of the guidewire, when the flap is deformed at the time when the guidewire is exposed to outside of the sheath from the lumen through the slit.

DETAILED DESCRIPTION OF THE INVENTION

First Embodiment

A first embodiment of the present invention will be described.

An endoscopic treatment tool according to the present embodiment is a catheter that can be inserted into a treatment tool channel of an endoscope.

Figure 1:
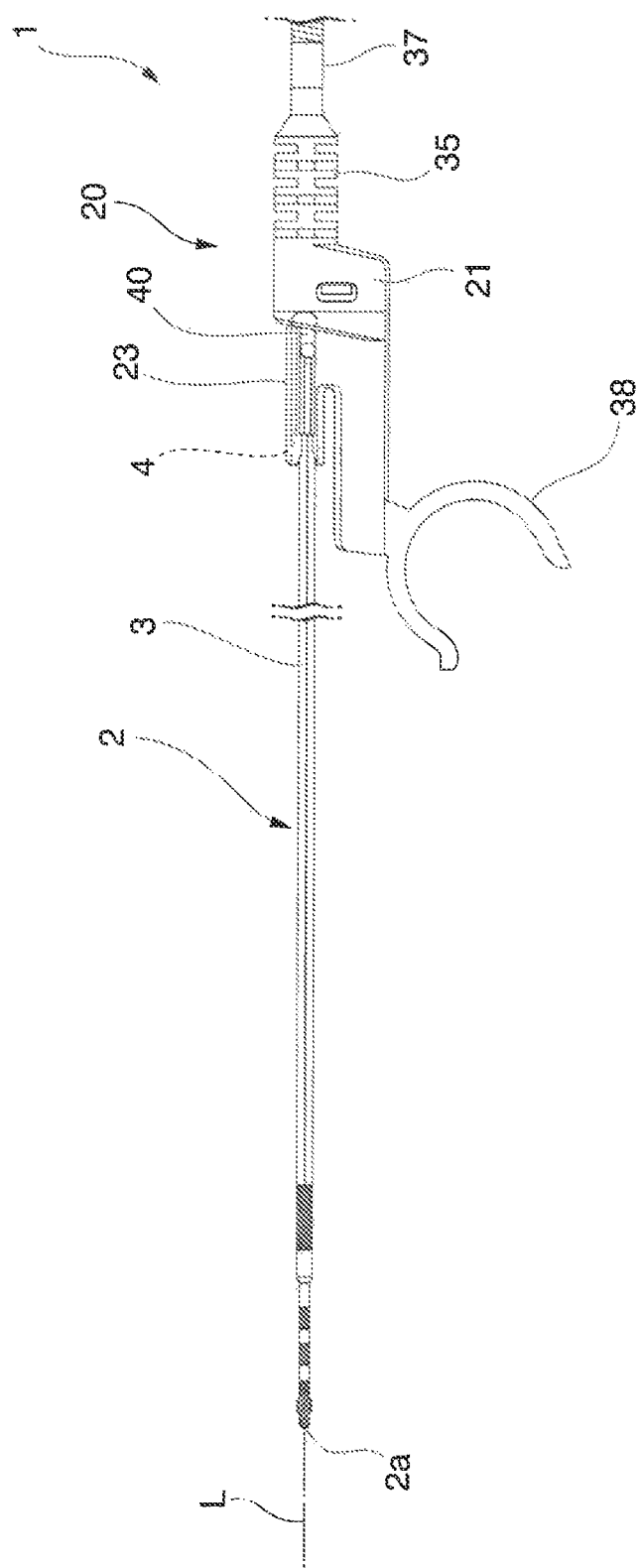
FIG. 1 is an overall view showing an endoscopic treatment tool according to a first embodiment of the present invention.
Figure 2:
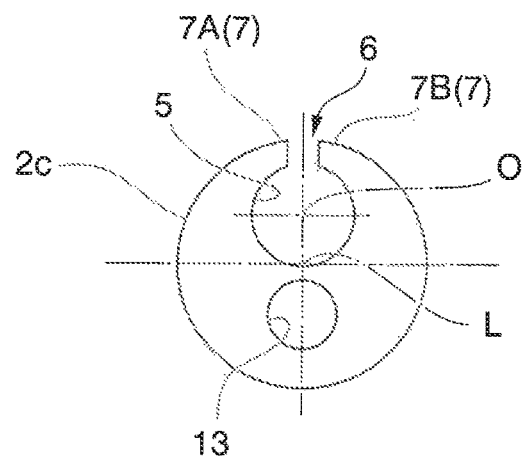
FIG. 2 is a view showing a cross section of a sheath of the endoscopic treatment tool in a radial direction.
Figure 3:
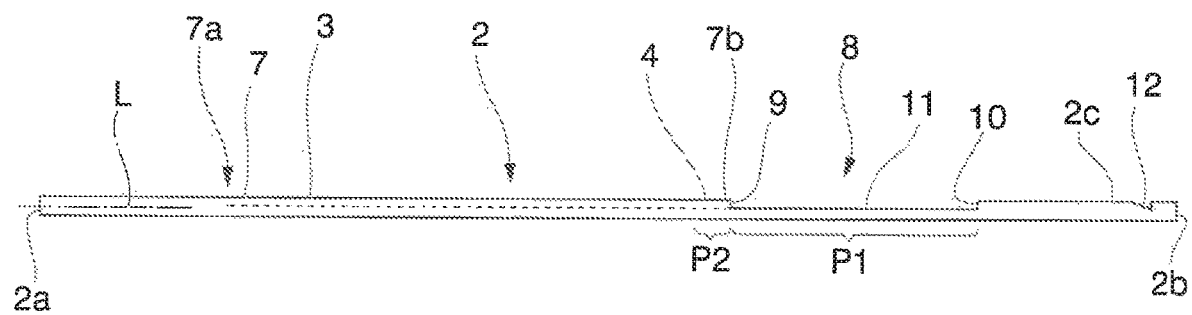
FIG. 3 is a lateral view of the sheath.
Figure 4:
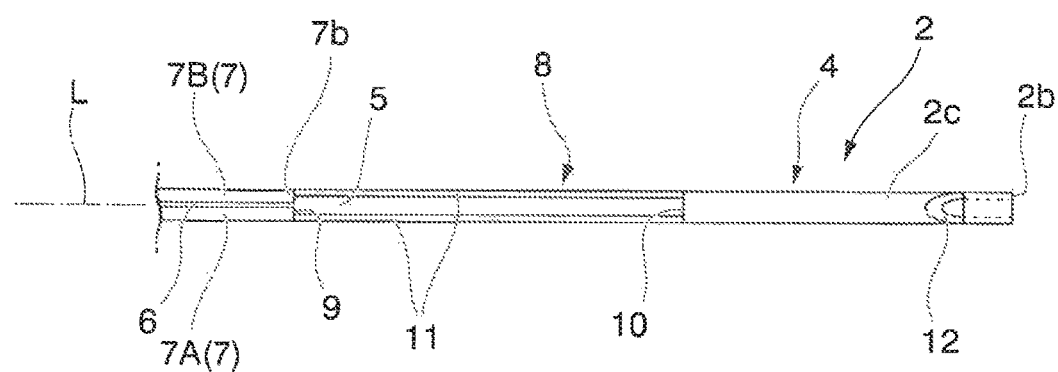
FIG. 4 is a plan view of the sheath.
Figure 5:
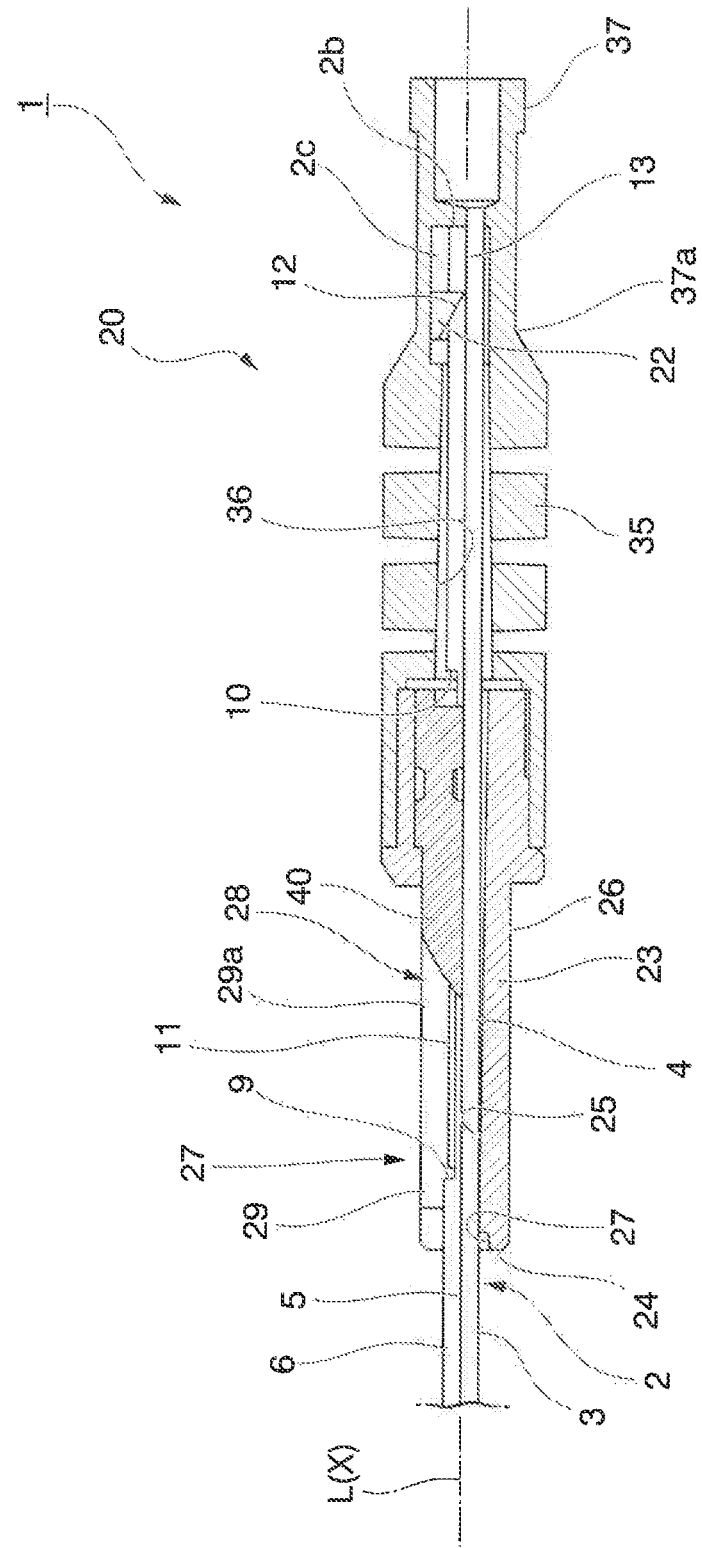
FIG. 5 is a cross-sectional view of an operation portion of the endoscopic treatment tool.

FIG. 1 is an overall view showing the endoscopic treatment tool according to the present embodiment. FIG. 2 a view showing a cross section of a sheath of the endoscopic treatment tool in a radial direction. FIG. 3 is a lateral view of the sheath. FIG. 4 is a plan view of the sheath. FIG. 5 is a cross-sectional view of an operation portion of the endoscopic treatment tool.

As shown in FIG. 1, a catheter 1 includes a sheath 2 and an operation portion 20.

The sheath 2 is a flexible elongated member having a longitudinal axis L. The sheath 2 has a distal region 3 including a distal end and a proximal region 4 including a proximal end. The proximal region 4 of the sheath 2 is inserted into a port 23 of the operation portion 20 to be fixed to the operation 20.

As shown in FIG. 2 to FIG. 4, the sheath 2 has a guidewire lumen 5, a notch 8, a slip preventing member 12, and a liquid lumen 13.

As shown in FIG. 5, the proximal region 4 of the sheath 2 according to the present embodiment is a region inside the port 23 that will be described later and a region more proximal than the port 23. The distal region 3 of the sheath 2 according to the present embodiment is a region continuing from the proximal region 4 and extending to the outside of the port 23.

The guidewire lumen 5 opens at a distal end 2a and a proximal end 2b of the sheath 2. In a section cross view of the sheath 2 in a radial direction, the guidewire lumen 5 is formed with a circular shaped internal surface having a diameter larger than an external diameter of a guidewire W. Further, a slit 6 is formed in the guidewire lumen 5 such that the slit 6 extends between a position 7a proximally spaced apart from the distal end 2a of the sheath 2 and a position 7b proximally spaced apart from the position 7a. However, the slit 6 is not limited thereto, and the slit 6 may extend from the distal end 2a to the proximal end 2b of the sheath 2. The guidewire lumen 5 opens on an external peripheral surface 2c of the sheath 2 via the slit 6. The slit 6 is formed to continue from the guidewire lumen 5 to the outside of the sheath 2.

As shown in FIG. 2, in the cross-sectional view of the sheath 2 in the radial direction, a width of the slit 6 of the sheath 2 is smaller than the diameter of the guidewire W. In the present embodiment, the slit 6 is formed by a pair of flaps 7 (first flap 7A and second flap 7B) facing each other in the circumferential direction of the sheath 2.

As shown in FIG. 3, the flap 7 according to the present embodiment has a distal end 7a in the distal region 3 of the sheath 2 and a proximal end 7b in the proximal region of the sheath 2. As shown in FIG. 3, for example, a position of the distal end 7a of the flap 7 is proximally spaced apart from the distal end 2a of the sheath 2. The flap 7 is configured to extend from the distal end 2a of the sheath 2 toward the proximal region 4 of the sheath 2 along the longitudinal axis L.

In FIG. 1, the distal end of the catheter 1 is formed to have a tapered shape suitable for the treatment, however, in FIG. 3, the tapered shape of the distal end is omitted.

As shown in FIGS. 3 and 4, the notch 8 is disposed in the proximal region 4 of the sheath 2. The notch 8 has a distal end surface 9, a proximal end surface 10, and a notch surface 11.

The distal end surface 9 and the proximal end surface 10 of the notch 8 are surfaces orthogonal to the longitudinal axis L of the sheath 2.

The distal end surface 9 of the notch 8 is formed to face the proximal end 2b of the sheath 2. The position of the distal end surface 9 of the notch 8 coincides with that of the flap 7. As shown in FIG. 5, in the state in which the proximal region 4 of the sheath 2 is fixed to the operation portion 20, the distal end surface 9 of the notch 8 is positioned more proximal than a distal opening 27 of the port 23.

As shown in FIG. 3 and FIG. 4, the proximal end surface 10 is formed to face the distal end 2a of the sheath 2. The position of the proximal end surface 10 of the notch 8 is more distal than that of the proximal end 2b of the sheath 2 and more proximal than that of the distal end surface 9 of the notch 8.

The notch surface 11 is formed in a shape such that the flap 7 is cut off between the distal end surface 9 and the proximal end surface 10 of the notch 8 along the longitudinal axis L of the sheath 2. The notch surface 11 according to the present embodiment is formed at two places spaced apart from each other such that the guidewire lumen 5 is sandwiched therebetween. The notch surface 11 can come in contact with the rotation preventing member 40 that will be described later. In the cross-sectional view of the sheath 2 in the radial direction, the internal surface of the guidewire lumen 5 that is sandwiched by the notch surface 11 is cutoff such that half or less of the entire circumference of the guidewire lumen 5 remains.

The slip preventing member 12 is formed at a position more proximal than the notch 8. In the state in which the sheath 2 is attached to the operation portion 20, the slip preventing member 12 is positioned more proximal than the port 23. The slip preventing member 12 is formed to be recessed from the external peripheral surface 2c of the sheath 2 in order to lock the sheath 2 with respect to the operation 20 by inserting a projection formed in the operation portion 20 that will be described later into the slip preventing member 12.

The liquid lumen 13 shown in FIG. 2 opens at the distal end 2a and the proximal end 2b of the sheath 2 (see FIG. 3). The liquid lumen 13 is configured to transport a liquid such as a contrast medium from the proximal end 2b to the distal end 2a of the sheath 2.

Figure 6:
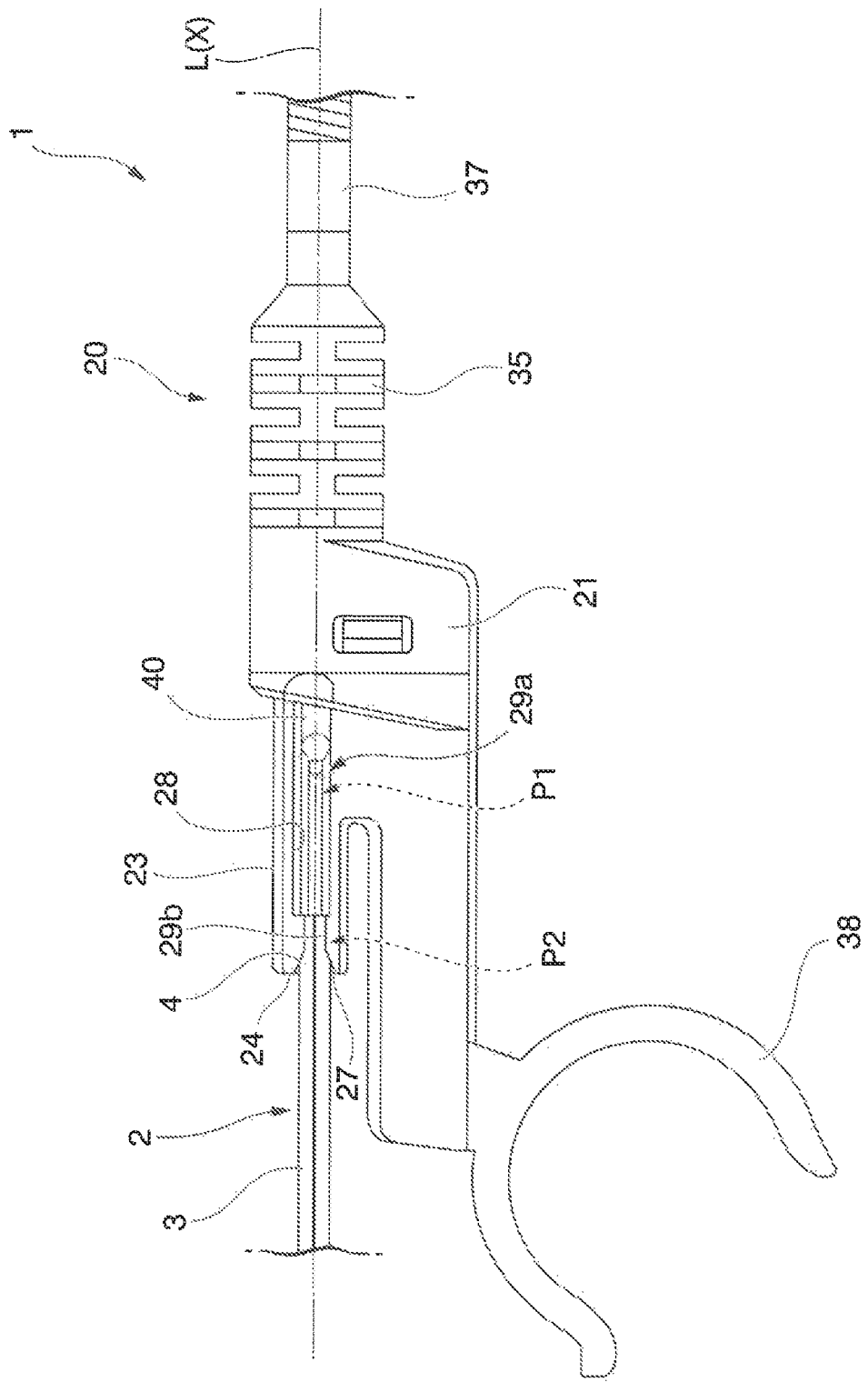
FIG. 6 is a lateral view of the operation portion.

FIG. 6 is a lateral view of the operation portion.

As shown in FIG. 1, FIG. 5 and FIG. 6, the operation portion 20 has a main body 21, a port 23, a bending preventing member 35, an adaptor 37, a hook 38, and a rotation preventing member (rotation preventing portion) 40.

As shown in FIG. 5, the main body 21 has a space into which the proximal region 4 of the sheath 2 is inserted.

As shown in FIG. 5 and FIG. 6, the port 23 forms an almost tubular shape such that a center line X becomes straight. The port 23 according to the present embodiment is connected to the main body 21.

According to the present embodiment, the proximal region 4 of the sheath 2 is the part inserted into the port 23 and the region more proximal than this part among the sheath 2. The proximal region 4 of the sheath 2 is formed to be straight since the center line X of the port 23 is straight. The port 23 is fixed to the proximal region 4 of the sheath 2 since the sheath 2 is fixed to the main body 21.

Figure 7:
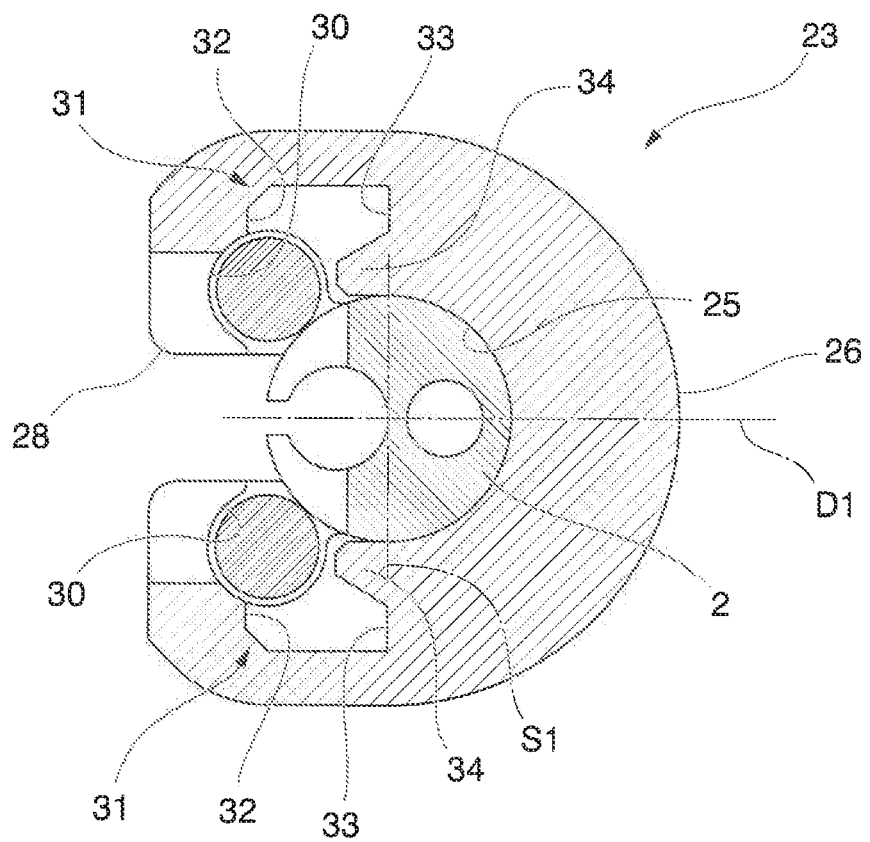
FIG. 7 is a view showing a cross section of the operation portion in a radial direction.
Figure 8:
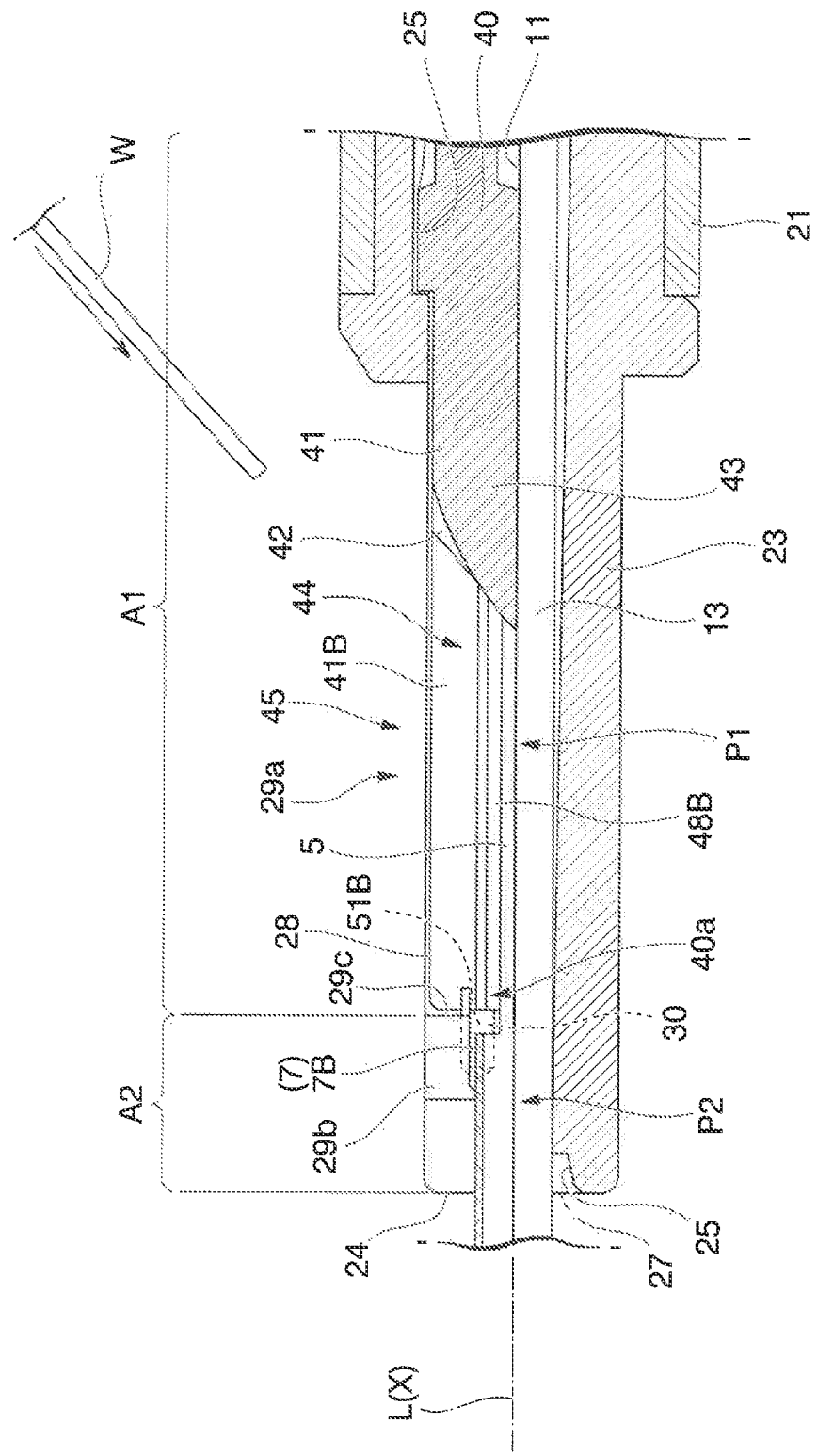
FIG. 8 is a view showing a cross section taken along a center line of a port in the lateral view of the operation portion.
Figure 9:
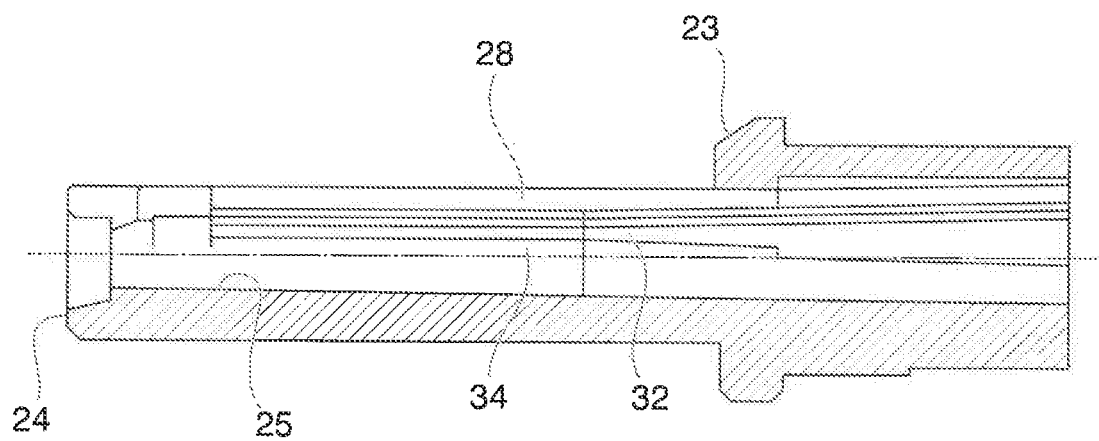
FIG. 9 is an enlarged cross-sectional view of the port.

FIG. 7 is a cross-sectional view of the operation portion in the radial direction. FIG. 8 is a view showing a cross section taken along the center line of the port in the lateral view of the operation portion. FIG. 9 is an enlarged cross-sectional view of the port.

As shown in FIG. 6 and FIG. 7, the port 23 has a distal end surface 24, an internal surface 25, an external surface 26, a distal end opening 27, a lateral opening 28, and a groove 31. In the present description, both the distal end opening 27 and the lateral opening 28 are referred to an opening of the port 23.

As shown in FIG. 6 and FIG. 8, the distal end opening 27 of the port 23 opens at the distal end surface 24 of the port 23. The sheath 2 is inserted into the distal end opening 27. The distal end opening 27 communicates with the lateral opening 28. The part of the internal surface 25 of the port 23 located in the distal end opening 27 is formed in a tapered shape such that an opening width of the port 23 becomes larger toward the distal end.

The lateral opening 28 of the port 23 opens at the lateral side of the port 23 such that the internal surface 25 of the port 23 communicates with the external surface 26 of the port 23. The lateral opening 28 is formed to extend from the distal end surface 24 of the port 23 toward the proximal side of the port 23 in the longitudinal axis direction of the port 23. Part of the rotation preventing member 40 enters the lateral opening 28 of the port 23.

As shown in FIG. 3, FIG. 6 and FIG. 8, in a region of the port 23 where the lateral opening 28 is formed, a range (first range A1) where the rotation preventing member 40 is arranged includes a part (first region P1) where the notch surface 11 of the sheath 2 is formed, and an entry port 29a for inserting the guidewire W into the guidewire lumen 5 and removing the guidewire W from the guidewire lumen 5 is formed in the range.

In the region of the port 23 where the lateral opening 28 is formed, a predetermined range (second range A2) at the distal end side of the port 23 includes a part (second region P2) formed in a substantially tubular shape and more distal than the notch 8 of the sheath 2 and part of the first region in the distal end side, and a slot 29b having a diameter larger than that of the outer diameter of the guidewire W is formed such that the guidewire W can be exposed to the outside from the guidewire lumen 5 via the lateral opening 28. A proximal end of the second region A2 in the port 23 is positioned more proximally than the proximal end of the flap 7.

At the proximal end 29c of the second region A2 in the port 23, a receiving portion 30 (receiving portion 30A, receiving portion 30B) is formed to be inserted by an elastic portion 51 that will be described later. In a state in which a part of the external peripheral of the elastic portion 51 is exposed to the outside toward the sheath 2, the receiving portion 30 is configured to hold the other part of the external peripheral of the elastic portion 51 such that the elastic portion 51 can come in contact with the flap 7 of the sheath 2.

As shown in FIG. 8, in the second range A2, the internal surface 25 (the slot 29 included) of the port 23 is connected to the distal end opening 27 and formed in a tapered shape such that the inner diameter thereof gradually becomes larger toward the distal end surface 24.

As shown in FIG. 7, the groove 31 is formed on the internal surface 25 of the port 23 for determining a position of the rotation preventing member 40 with respect to the port 23. The groove 31 is configured to include a first groove 32 which is formed along a first plane S1 orthogonal to a direction of a straight line (an opening direction D1 of the lateral opening 28) which is orthogonal to the longitudinal axis L of the sheath 2 and passes through the lateral opening 28 of the port 23, in the cross-sectional view of the port 23 in the radial direction, and a second groove 33 which is formed to extend in a direction orthogonal to the first plane from an end portion of the first groove 32.

The first groove 32 is formed in two places spaced apart from each other to sandwich the sheath 2 therebetween, when viewed from the opening direction D1 of the lateral opening 28. In the same way, the second groove 33 is formed in two places spaced apart from each other to sandwich the sheath 2 therebetween, when viewed from the opening direction D1 of the lateral opening 28.

When viewed from the opening direction D1 of the lateral opening 28, a protrusion shape portion 34 configured for engaging with a rail 45 of an arm 44 of the rotation preventing member 40 is formed at a position closer to the sheath 2 than the second groove 33.

Each of the first groove 32, the second groove 33 and the protrusion shape portion 34 extends in the direction of the center line X of the port 23 (see FIG. 9).

As shown in FIG. 5, the bending preventing member 35 is a flexible tubular portion having a conduit 36 into which the proximal region 4 of the sheath 2 is inserted for connecting the liquid lumen 13 with the adaptor 37.

The adaptor 37 is formed at the proximal end of the bending preventing member 35. A well-known syringe can be connected to the adaptor 37. For example, it is possible to connect a syringe having liquid such as the contrast medium to the adaptor 37 and transport the liquid such as the contrast medium to the liquid lumen 13 from the syringe via the adaptor 37 and the conduit 36 inside the bending preventing member 35.

In the present embodiment, a protrusion 22 entering the slip preventing member 12 of the sheath 2 is disposed near the distal end portion 37a of the adaptor 37.

As shown in FIG. 6, the hook 38 is formed in a substantial C shape for connecting the operation portion 20 of the catheter 1 according to the present embodiment to an operation portion and the like of a well-known endoscope. By attaching the hook 38 to the operation portion of the endoscope such that the hook 38 grasps the external peripheral surface of the endoscope, an operator can use both of the endoscope and the catheter 1 by holding the operation portion of the endoscope without holding the operation portion 20 of the catheter 1.

As shown in FIG. 8, the rotation preventing member 40 is disposed between the notch surface 11 and the internal surface 25 of the port 23. The rotation preventing member 40 has a root portion 41 and the arm 44. In the present embodiment, the root portion 41 and the arm 44 are integrally formed. A material used for forming the rotation preventing member 40 can be the resin material, for example. The rotation preventing member 40 may have a different color from that of the port 23 such that it is easy to identify the position of the lateral opening 28 of the port 23.

Figure 10:
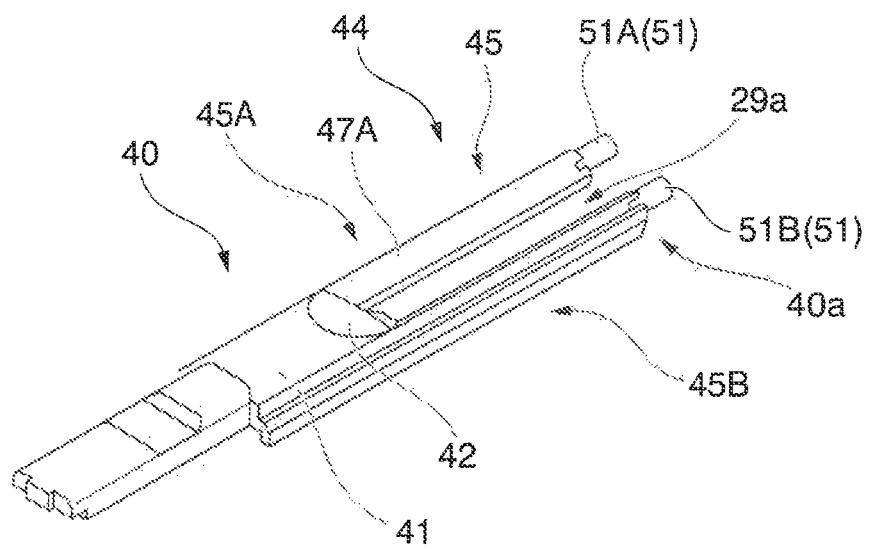
FIG. 10 is an oblique view showing a rotation preventing member of the endoscopic treatment tool.
Figure 11:
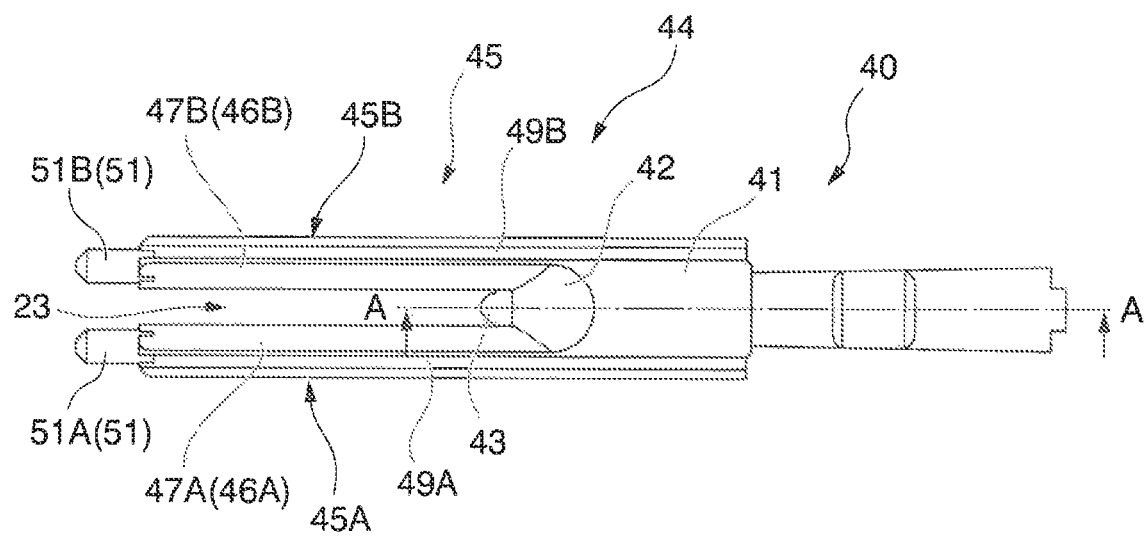
FIG. 11 is a plan view of the rotation preventing member.
Figure 12:
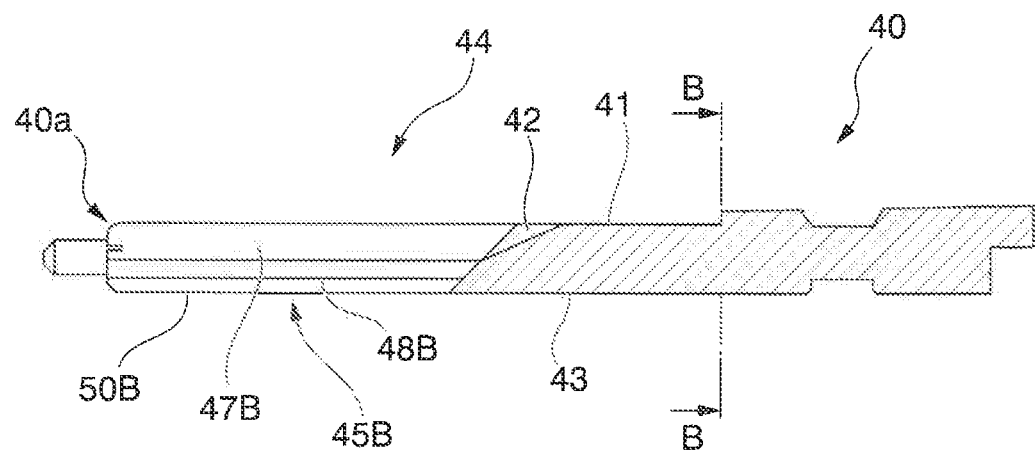
FIG. 12 is a cross-sectional view taken along line A-A in FIG. 11.

FIG. 10 is an oblique view showing the rotation preventing member of the endoscopic treatment tool. FIG. 11 is a plan view of the rotation preventing member. FIG. 12 is a cross-sectional view taken along line A-A in FIG. 11.

As shown in FIG. 10 to FIG. 12, the root portion 41 has an opening proximal portion 42 and a key 43.

As shown in FIG. 8, the opening proximal portion 42 is formed in a tapered shape for guiding the guidewire W to the guidewire lumen 5 positioned between the notch surfaces 11 formed in the sheath 2. For example, the opening proximal portion 42 is curved in a tapered shape to form part of a lateral surface of a circular truncated cone such that a diameter close to the external surface 26 of the port 23 is relatively large and a diameter close to the internal surface 25 of the port 23 is relatively small. The surface having the tapered shape of the opening proximal portion may be formed from a plane. The opening proximal portion 42 is configured to form an edge of the opening (the entry port 29a) for inserting the guidewire W into the guidewire lumen 5 and removing the guidewire W from the guidewire lumen 5. The entry port 29a may be processed to improve the sliding property between the guidewire W and the entry port 29a to make it easier to insert and remove the guidewire W. For example, the material of the rotation preventing member 40 forming the entry port 29a is the polyacetal resin (POM). The surface roughness (Ra) of the opening proximal portion 42 forming the entry port 29a, and an opening lateral portions 46A and 46B which will be described later is equal to or less than 0.25. The surface processing with respect to the opening proximal portion 42 forming the entry port 29a, and the opening lateral portions 46A and 46B which will be described later can be the fluorine-based lubrication painting.

As shown in FIG. 8, the key 43 is disposed inside the guidewire lumen 5 in a state in which the rotation preventing member 40 is attached to the notch 8. The key 43 is configured to prevent the relative rotation between the rotation preventing member 40 and the sheath 2 while filling the guidewire lumen 5 for preventing the guidewire W from entering the proximal end side of the guidewire lumen 5 beyond the root portion 41.

Figure 13:
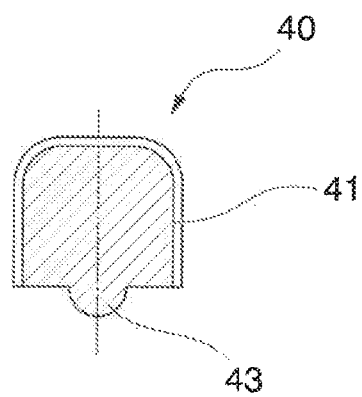
FIG. 13 is a cross-sectional view taken along line B-B in FIG. 12.
Figure 14:
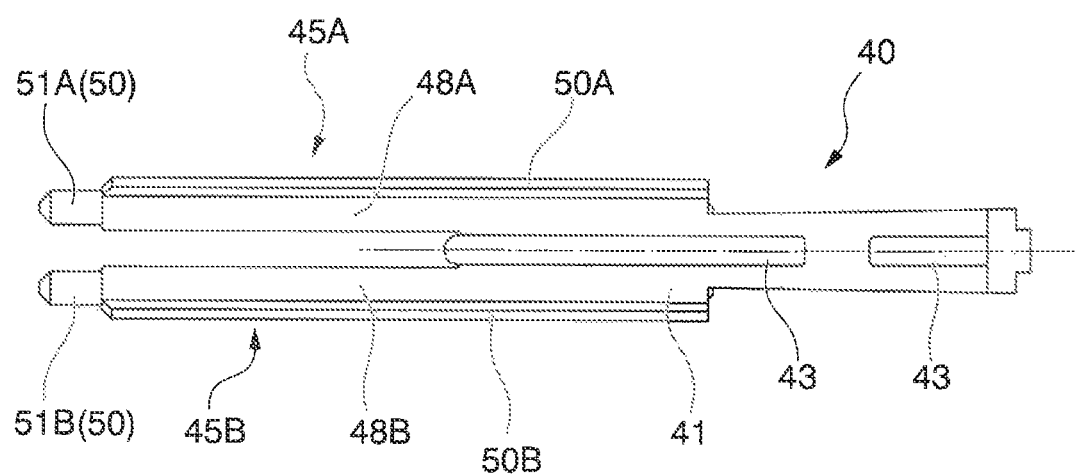
FIG. 14 is a bottom view of the rotation preventing member.
Figure 15:
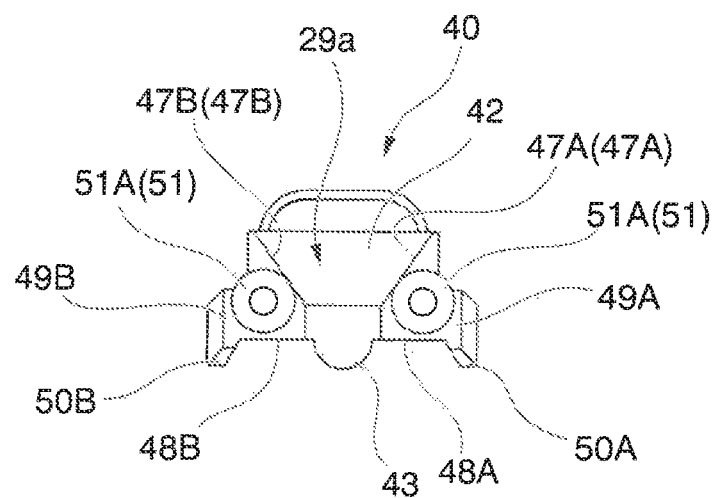
FIG. 15 is a front view of the rotation preventing member.
Figure 16:
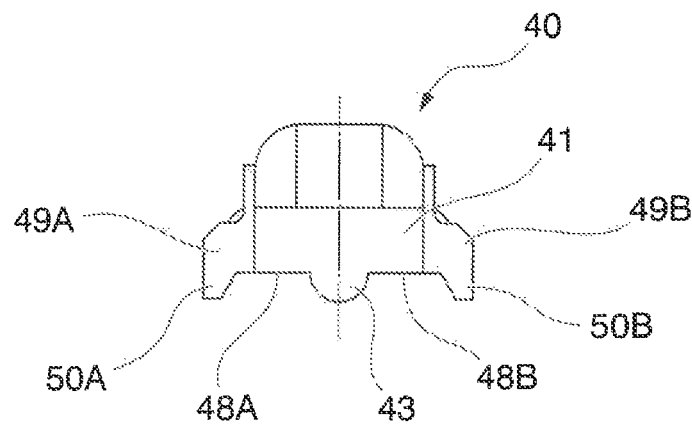
FIG. 16 is a rear view of the rotation preventing member.

FIG. 13 is a cross-sectional view taken along line B-B in FIG. 12. FIG. 14 is a bottom view of the rotation preventing member. FIG. 15 is a front view of the rotation preventing member. FIG. 16 is a rear view of the rotation preventing member.

As shown in FIG. 10 to FIG. 16, the arm 44 has the rail 45 and the elastic portion 51.

The rail 45 has a first rail 45A and a second rail 45B which have symmetrical shapes with each other. In the following description, only the configuration of the first rail 45A will be described, and because the second rail 45B has the symmetrical shape with the first rail 45A, the detailed description of the configuration of the second rail 45B will be omitted.

The first rail 45A has the opening lateral portion 46A, an engaging surface 48A, a first protrusion 49A and a second protrusion 50A.

The opening lateral portion 46A has an inclined surface 47A for guiding the guidewire W (see FIG. 8) to the guidewire lumen 5. The opening lateral portion 46A is configured to form the border of the opening (the entry port 29a) for inserting the guidewire W into the guidewire lumen 5 and removing the guidewire W from the guidewire lumen 5.

Figure 17:
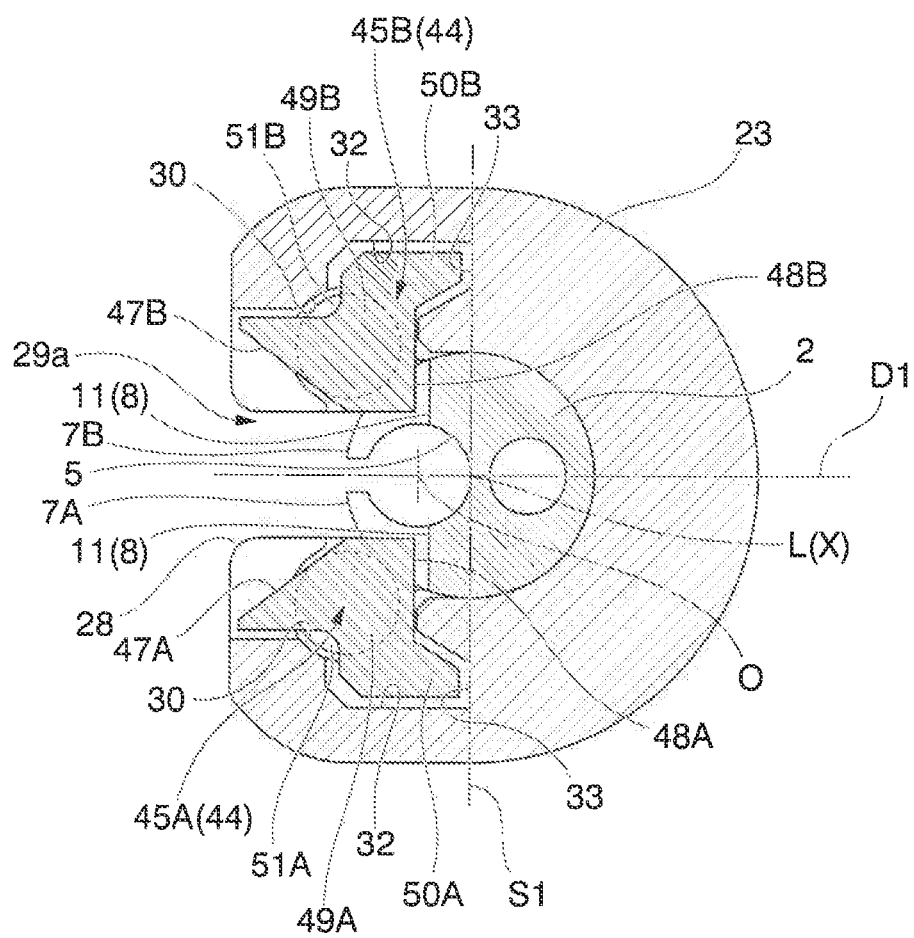
FIG. 17 is a cross-sectional view in the radial direction showing a state in which the rotation preventing member is attached to the port.

FIG. 17 is a cross-sectional view in the radial direction showing a state in which the rotation preventing member is attached to the port.

As shown in FIG. 17, the engaging surface 48A is a surface facing the notch surface 11 formed in the notch 8 of the sheath 2. In the state in which the rotation preventing member 40 is attached to the port 23, the engaging surface 48A extends in the direction of the center line X (see FIG. 8) of the port 23. The engaging surface 48A can come in contact with the notch surface 11 formed in the notch 8 of the sheath 2. The engaging surface 48A comes in contact with the notch surface 11 so as to restrict the notch surface 11 from moving in to the rotation direction around the longitudinal axis L of the sheath 2. As shown in FIG. 17, the rotation preventing member 40 has a gap communicating with the opening of the port 23.

The first protrusion 49A is configured to extend in the direction of the center line X of the port 23 to be fitted into the first groove 32. The first protrusion 49A is configured to hold the first rail 45A in the port 23 such that the first rail 45A does not slip out from the lateral opening 28 of the port 23.

The second protrusion 50A is formed to be fitted into the second groove 33 of the port 23 and connected to the first protrusion 49A. The second protrusion 50A is configured to extend in the direction of the center line X (see FIG. 8) of the port 23, in a state in which the rotation preventing member 40 is attached to the port 23. The second protrusion 50A is configured to hold the first rail 45A so as to maintain the state in which the first rail 45A is parallel to the center line X of the port 23.

Same as the first rail 45A, the second rail 45B has an opening lateral portion 46B, an engaging surface 48B, a first protrusion 49B, and a second protrusion 50B.

As shown in FIG. 10 and FIG. 11, the elastic portion 51 is disposed at each of the distal ends of the first rail 45A and the second rail 45B. The elastic portion 51 is arranged in the second region in the proximal region 4 of the sheath 2. As shown in FIG. 8, the elastic portion 51 can come in contact with the flap 7 of the external peripheral surface 2c of the sheath 2 in the second region P2.

The elastic portion 51A disposed at the distal end of the first rail 45A can come in contact with the first flap 7A of the sheath 2. The elastic portion 51B disposed at the distal end of the second rail 45B can come in contact with the second flap 7B of the sheath 2.

As shown in FIG. 17, the elastic portion 51 is arranged at a position closer to the lateral opening 28 of the port 23 with respect to the center axis O of the guidewire lumen 5. In a side view in the direction of the straight line (the opening direction D1 of the lateral opening 28) which is orthogonal to the longitudinal axis L of the sheath 2 and passes through the lateral opening 28 of the port 23, the two elastic portions 51 are disposed at positions spaced apart from each other in the radial direction of the sheath 2. The elastic portion 51 is formed in a column shape to have a center line extending in the direction of the center line X of the port 23. The outer diameter of the elastic portion 51 is smaller than the inner diameter of the receiving portion 30 formed in the port 23. Accordingly, the elastic portion 51 can be inserted into the receiving portion 30, and the elastic portion 51 can move inside the receiving portion 30 when the elastic portion 51 comes in contact with the flap 7. The elastic portion 51 is configured to push the flap 7 back to the original position due to the elastic property of the arm 44 after the elastic portion 51 comes in contact with the flap 7 and moves.

According to the present embodiment, in the state in which the elastic portion 51 is inserted into the receiving portion 30, the rotation preventing member 40 is connected to the port 23 by the elastic portion 51 and the receiving portion 30 such that there is no significant misalignment between the position of the distal end of the rotation preventing member 40 and the position of the port 23.

According to the present embodiment, the configuration in which the rotation preventing member 40 and the elastic portion 51 are formed as the same member is described; however, the elastic portion may be independently formed as another member. In this case, the elastic portion 51 may be formed using an elastic material such as a silicone rubber and the like. when the elastic material is used, like the elastic portion 51 according to the present embodiment, after removing the guidewire W from the guidewire lumen 5, it is possible to push the flap 7 back to the original position due to the elastic property of the elastic material with which the flap 7 comes in contact (not shown).

Figure 18:
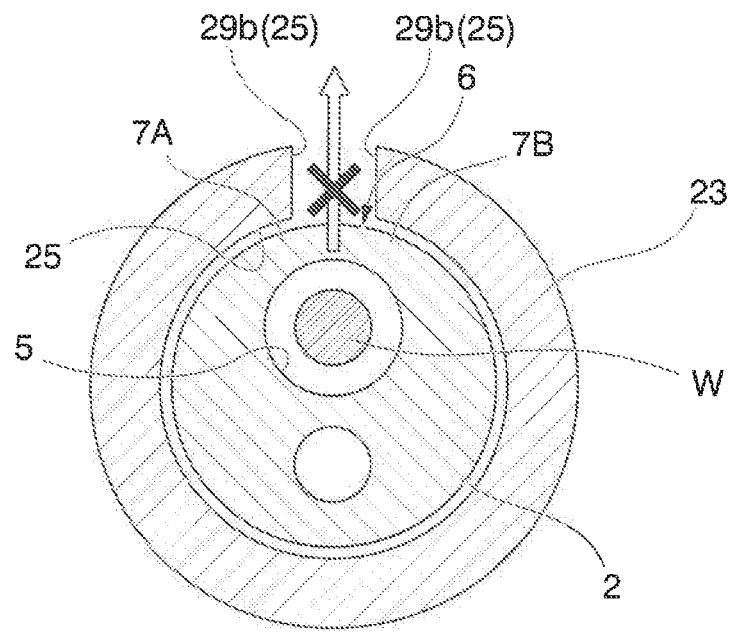
FIG. 18 is a schematic view showing an effect of the endoscopic treatment tool.
Figure 19:
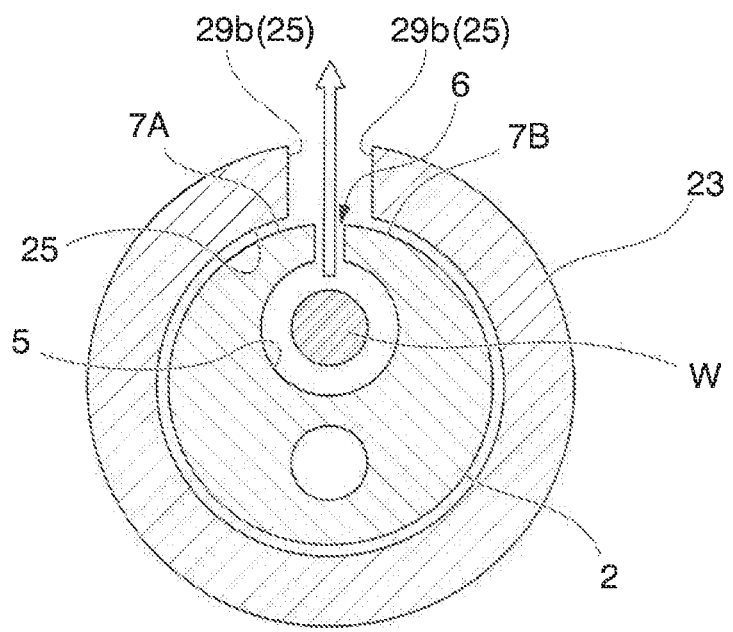
FIG. 19 is a schematic view showing the effect of the endoscopic treatment tool.
Figure 20:
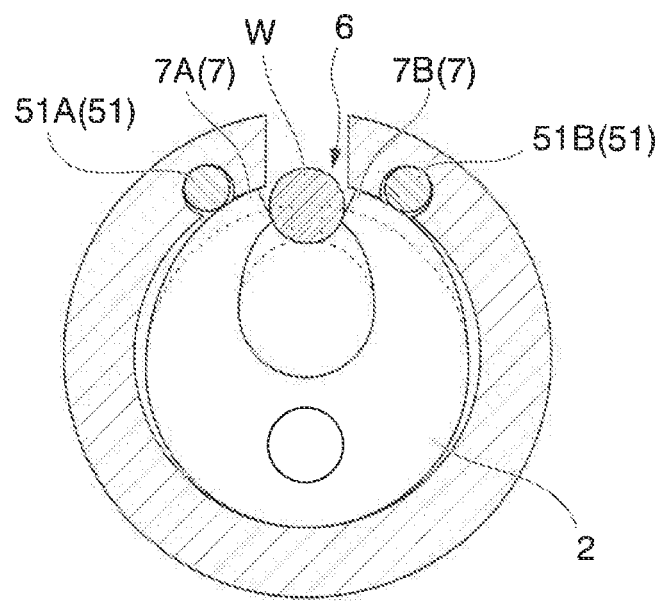
FIG. 20 is a schematic view showing the effect of the endoscopic treatment tool.

Effects of the catheter 1 according to the present embodiment will be described. FIG. 18 is a schematic view showing the effect of the endoscopic treatment tool. FIG. 19 is a schematic view showing the effect of the endoscopic treatment tool. FIG. 20 is a schematic view showing the effect of the endoscopic treatment tool.

According to the present embodiment, as shown in FIG. 17, the notch surface 11 of the sheath 2 and the engaging surfaces 48A and 48B of the rotation preventing member 40 can come in contact with each other such that the sheath 2 does not rotate inside the port 23. That is, even if a torsion around the longitudinal axis L of the sheath 2 as the center occurs in the distal region 3 of the sheath 2, the torsion of the sheath 2 will not be transmitted from the distal end 40a (see FIG. 8) of the rotation preventing member 40 toward the proximal side. Accordingly, it is possible to smoothly insert the guidewire W into the guidewire lumen 5 via the lateral opening 28 of the port 23.

In the state in which the guidewire W is inserted into the guidewire lumen 5 and the guidewire W is to be removed from the guidewire lumen 5, it is possible to expose the guidewire W from the guidewire lumen 5 via the slit 6. At this time, in the catheter 1 according to the present embodiment, even if the torsion of the sheath 2 occurs in the distal region 3 of the sheath 2, the torsion can be suppressed at a position in the vicinity of the proximal end of the flap 7 in the sheath 2 due to the distal end 40a of the rotation preventing member 40.

For example, as shown in FIG. 18, in a case when the torsion of the sheath 2 with respect to the port 23 occurs and the guidewire W is exposed from the guidewire lumen 5, there is a case in which the proximal end of the flap 7 is sandwiched between the guidewire W and the internal surface 25 of the port 23 (in the FIG. 18, the first flap 7A is easy to be sandwiched between the guidewire W and the slot 29b). In this case, the resistance generated when the guidewire W is exposed from the guidewire lumen 5 is increased due to the flap 7 that is sandwiched between the guidewire W and the internal surface 25 of the port 23.

On the other hand, as shown in FIG. 19, it is possible to suppress the situation in which the flap 7 is sandwiched between the guidewire W and the internal surface 25 of the port 23 and thus the guidewire W is not easily to be exposed, since the torsion of the sheath 2 at the position in the vicinity of the proximal end of the flap 7 is suppressed by the rotation preventing member 40.

Further, in a state in which the proximal end of the flap 7 is sandwiched between the guidewire W and the internal surface 25 of the port 23 and the guidewire W is forced to be exposed, the plastic deformation that occurs at the proximal end of the flap 7 will cause the operability to become worse when a re-insertion of the guidewire W into the guidewire lumen 5 or a similar operation is performed. According to the present embodiment, the plastic deformation at the proximal end of the flap 7 does not easily occur such that the insertion of the guidewire W into the guidewire lumen 5 can be rapidly performed.

As shown in FIG. 20, once the flap 7 is deformed when the guidewire W is exposed to the outside of the sheath 2 from the guidewire lumen 5 via the slit 6, the elastic portion 51 biases the flap 7 inward in the radial direction such that the width of the slit 6 becomes smaller than the outer diameter of the guidewire W. Accordingly, the first flap 7A and the second flap 7B are restored to the original positions by the elastic portion 51 such that the gap between the first flap 7A and the second flap 7B at the proximal end of the flap 7 becomes smaller than the outer diameter of the guidewire W.

As shown in FIG. 6, since the internal surface 25 (the slot 29b included) is formed in the tapered shape such that an opening width of the port 23 becomes larger toward the distal end, even if the sheath 2 is in the twisted state between the distal end of the arm 44 and the distal end surface 24 of the port 23, it is possible to expose the guidewire W from the slit 6 of the sheath 2 via the lateral opening 28 of the port 23 and the flap 7 of the sheath 2 does not interfere.

Second Embodiment

A second embodiment of the present invention will be described. In the present embodiment, elements that are same as those of the first embodiment will have the same reference signs of the first embodiment, and duplicate description will be omitted.

Figure 21:
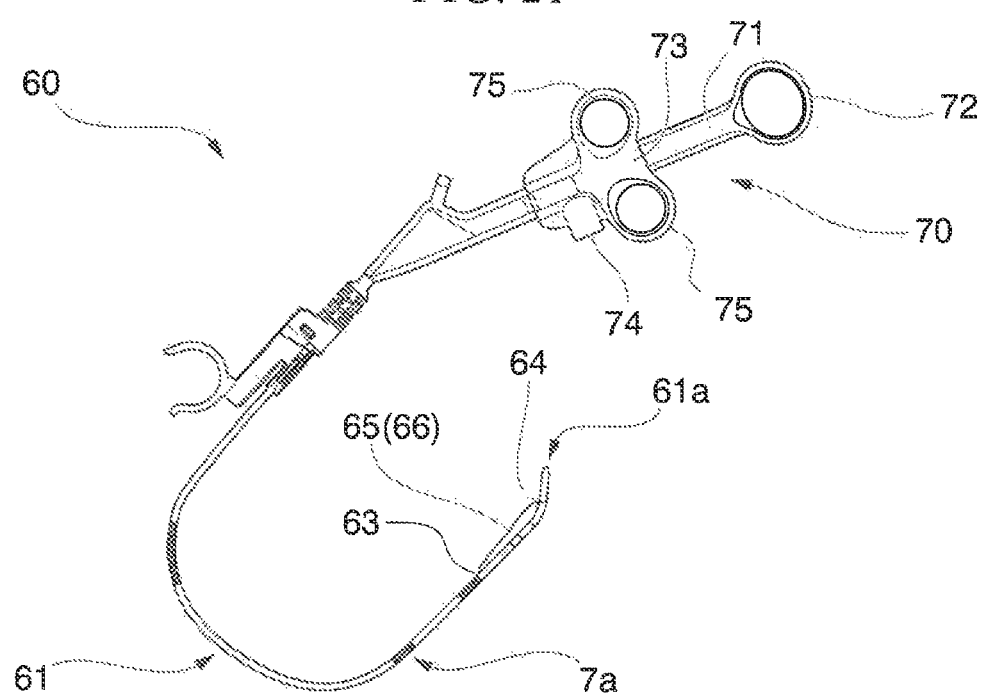
FIG. 21 is an overall view showing an endoscopic treatment tool according to a second embodiment of the present invention.
Figure 22:
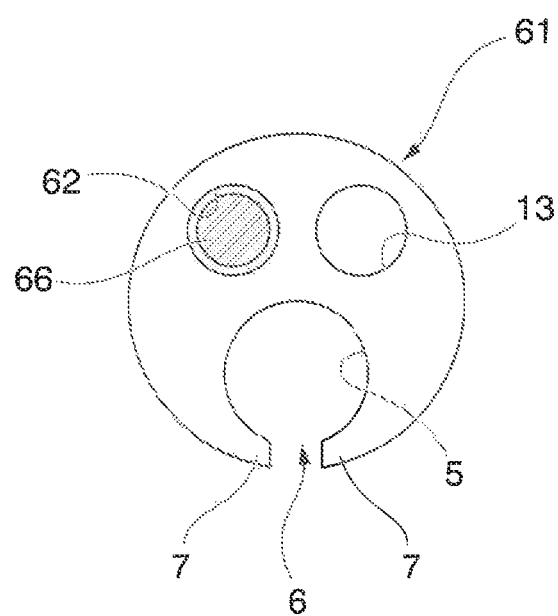
FIG. 22 is a view showing a cross section of a sheath of the endoscopic treatment tool in a radial direction.

FIG. 21 is an overall view showing an endoscopic treatment tool according to the present embodiment. FIG. 22 is a cross-sectional view of the endoscopic treatment tool in a radial direction.

The endoscopic treatment tool according to the present embodiment is a dissecting tool having a cutter configured to dissect the living tissue and disposed at a distal end of a sheath, and the endoscopic treatment tool is the same as the catheter 1 according to the first embodiment in that it is capable of discharging a liquid such as a contrast medium from the distal end of the sheath via the liquid lumen.

As shown in FIG. 21 and FIG. 22, a dissecting tool 60 according to the present embodiment has a sheath 61 and an operation portion 70.

In addition to the guidewire lumen 5 and the liquid lumen 13 according to the first embodiment, the sheath 61 further has a knife-wire lumen 62 configured to be inserted by a knife wire 66 that is connected to the cutter.

The sheath 61 has a through-hole portion 63 configured to realize a state for exposing a part (the cutter 65) disposed in the vicinity of the distal end of the knife wire 66 from the sheath 61, and a fixing portion 64 disposed more distally than the through-hole portion 63 for fixing the distal end of the knife wire 66 to the sheath 61. According to the present embodiment, a curved shape may be applied to the vicinity of the distal end 61a of the sheath 61 for suitably guiding the distal end 61a of the sheath 61 toward the dissecting target during the dissecting procedure using the dissecting tool 60.

The cutter 65 is formed from the part in the vicinity of the distal end of the knife wire 66. The knife wire 66 is formed from a straight member having an elastic property such as stainless steel, a shape-memory alloy, and the like.

In addition to the main body 21, the port 23, the bending preventing member 35, the adaptor 37, the hook 38, and the rotation preventing member 40 included in the operation portion 20 of the catheter 1 according to the first embodiment, the operation portion 70 of the dissecting tool 60 according to the present embodiment further has a rod-shaped portion 71 extending from the main body 21 toward the proximal side, and a slider 73 connecting to the rod-shaped portion 71 so as to be slidable with respect to the rod-shaped portion 71.

A distal end of the rod-shaped portion 71 is connected to the main body 21. A proximal end of the rod-shaped portion 71 is provided with a ring 72 through which the fingers of the operator are passed.

The slider 73 is connected to the proximal end of the knife wire 66. The slider 73 has a plug 74 for flowing a high-frequency current to the knife wire 66. The knife wire 66 and the plug 74 are electrically connected. The slider 73 has two rings 75 through which the fingers of the operator are passed.

In the present embodiment, in the vicinity of the distal end 61a of the sheath 61, the slit 6 and the distal end 7a of the flap 7 are positioned more proximally than the part of the knife wire 66 (the cutter 65) that is exposed outside of the sheath 61 (see reference sign 7a in FIG. 21). In the region from the slit 6 and the distal end of the flap 7 to the distal end 61a of the sheath 61, the guidewire lumen 5 does not open at the lateral side of the sheath 61.

The dissecting tool 60 according to the present embodiment can bend the distal end 61a of the sheath 61 into an arcuate shape by pulling the knife wire 66 due to the operation at the slider 73 of the operation portion 20 by the operator. At this time, the cutter 65 in the knife wire 66 is tensioned in a straight shape. In this state, it is possible to dissect the tissue using the knife wire 66 by flowing the high-frequency current to the knife wire 66 and bringing the tissue in contact with the knife wire 66. The dissecting tool 60 according to the present embodiment can be suitably used in an Endoscopic Sphincterotomy procedures (EST) for dissecting the duodenal papilla after an ERCP procedures.

For example, firstly a cholangiopancreatography procedure is performed using the catheter 1 according to the first embodiment, then the catheter 1 is removed with the guidewire W remained in the body, and the operator subsequently inserts the guidewire W into the guidewire lumen 5 of the dissecting tool 60 according to the present embodiment and inserts the distal end 61a of the sheath 61 of the dissecting tool 60 into the duodenal papilla. In the present embodiment, the distal end of the guidewire W is already inserted into the biliary and pancreatic ducts during the ERCP procedures, and it is possible to leave the guidewire W in the body and easily remove the catheter for to exchange the dissecting tool 60.

According to the dissecting tool 60 of the present embodiment, like the catheter according to the first embodiment, it is easy to insert the guidewire W into the lumen into which the guidewire W is inserted and remove the guidewire W from the lumen.

The embodiments of the invention have been described above with reference to the drawings, but specific structures of the invention are not limited to the embodiments and may include various modifications without departing from the scope of the invention.

For example, the endoscopic treatment tool of the present invention is not limited to the catheter 1 according to the first embodiment and the dissecting tool 60 according to the second embodiment. For example, the spirit of the present invention can also be applied to the endoscopic treatment tool having a balloon, a basket, and the like that are used together with a guidewire.

Although preferred embodiments of the present invention have been described above, the present invention is not limited to these embodiments and modifications thereof. Additions, omissions, substitutions, and other changes of constituent components are possible without departing from the spirit of the present invention. The present invention is not limited by the foregoing description, but is only limited by the scope of the appended claims.

What is claimed is:

1. An endoscopic treatment tool, comprising:
 a port having an internal surface, an external surface, and a lateral opening formed to communicate the internal surface to the external surface;
 a sheath having a proximal region fixed inside the port and a distal region continuing to the proximal region to extend to the outside of the port, the sheath having a lumen formed with an inner diameter larger than an outer diameter of a guidewire;
 a flap having a distal end in the distal region and a proximal end in the proximal region, the flap extending in a longitudinal axis direction of the sheath from a distal end to a proximal end of the sheath, and a slit formed to communicate the lumen to an external side of the sheath;
 a notch surface formed in the sheath between the proximal end of the flap and the proximal end of the sheath to form an opening along the longitudinal axis of the sheath; and
 a rotation preventing portion having an engaging surface configured to engage with the notch surface, wherein:
 the port has a groove formed on the internal surface extending along a longitudinal axis of the port, the rotation preventing portion has a protrusion, and
when the protrusion is fitted in the groove, the engaging surface and the notch surface face each other.

2. The endoscopic treatment tool according to claim 1, wherein at least part of the rotation preventing portion is configured to form a border of the lateral opening of the port for inserting the guidewire into the lumen.

3. The endoscopic treatment tool according to claim 1,
wherein the proximal region of the sheath is formed in a straight shape,
wherein the lateral opening of the port is extended to a distal end surface of the port,
wherein the proximal region of the sheath includes
a first region in which the notch surface is formed; and
a second region formed in a substantial tubular shape from a distal end of the notch surface to the distal end surface of the port, and
wherein the second region is configured to communicate with the opening of the port in a radial direction of the sheath.

4. The endoscopic treatment tool according to claim 1, wherein the rotation preventing portion is configured to restrict a movement of the notch surface in a rotation direction around the longitudinal axis of the sheath.

5. The endoscopic treatment tool according to claim 1, wherein the rotation preventing portion has a gap communicating with the opening of the port.

6. The endoscopic treatment tool according to claim 1, wherein the rotation preventing portion has an elastic portion inserted into a space between an external peripheral surface of the sheath and the internal surface.

7. The endoscopic treatment tool according to claim 6, wherein:
the elastic portion is configured to extend between an external peripheral surface of a second region and the internal surface, and
the rotation preventing portion has the elastic portion that is positioned on both sides of the slit.

8. The endoscopic treatment tool according to claim 6, wherein the opening of the port is formed such that an opening width gradually increases toward the distal end surface of the port in a range more distal than a distal end of the elastic portion.

9. The endoscopic treatment tool according to claim 6,
wherein a width of the slit is smaller than the outer diameter of the guidewire, wherein at least part of the elastic portion is disposed at both sides of the slit at a position on a side of the opening of the port with respect to a center axis of the lumen, and wherein at least part of the elastic portion is configured to bias the flap inwardly in a radial direction such that the width of the slit becomes smaller than the outer diameter of the guidewire, when the guidewire is exposed to outside of the sheath from the lumen through the slit.

10. The endoscopic treatment tool according to claim 1, wherein the slit has a width smaller than a diameter of the lumen.

11. The endoscopic treatment tool according to claim 1, wherein the rotation preventing portion has an inclined surface inclined from the lateral opening toward the lumen when the protrusion is fitted in the groove.

* * * * *